(12) United States Patent
Koseoglu et al.

(10) Patent No.: US 10,794,821 B2
(45) Date of Patent: Oct. 6, 2020

(54) CHARACTERIZATION OF CRUDE OIL BY ULTRAVIOLET VISIBLE SPECTROSCOPY

(71) Applicants: Omer Refa Koseoglu, Dhahran (SA); Adnan Al-Hajji, Dhahran (SA); Gordon Jamieson, London (GB); Saudi Arabian Oil Company, Dhahran (SA)

(72) Inventors: Omer Refa Koseoglu, Dhahran (SA); Adnan Al-Hajji, Dhahran (SA); Gordon Jamieson, London (GB)

(73) Assignee: SAUDI ARABIAN OIL COMPANY, Dhahran (SA)

( * ) Notice: Subject to any disclaimer, the term of this patent is extended or adjusted under 35 U.S.C. 154(b) by 575 days.

(21) Appl. No.: 15/540,141

(22) PCT Filed: Jan. 5, 2016

(86) PCT No.: PCT/US2016/012167
§ 371 (c)(1),
(2) Date: Jun. 27, 2017

(87) PCT Pub. No.: WO2016/112002
PCT Pub. Date: Jul. 14, 2016

(65) Prior Publication Data
US 2017/0370830 A1 Dec. 28, 2017

Related U.S. Application Data

(60) Provisional application No. 62/099,669, filed on Jan. 5, 2015.

(51) Int. Cl.
*G01N 31/00* (2006.01)
*G01N 21/33* (2006.01)
(Continued)

(52) U.S. Cl.
CPC .......... *G01N 21/33* (2013.01); *G01N 21/314* (2013.01); *G01N 21/5907* (2013.01);
(Continued)

(58) Field of Classification Search
CPC .. G01N 21/33; G01N 21/314; G01N 21/5907; G01N 33/28; G01N 33/2823;
(Continued)

(56) References Cited

U.S. PATENT DOCUMENTS 3,617,501 A 11/1971 Eng
3,896,312 A 7/1975 Brown
(Continued)

FOREIGN PATENT DOCUMENTS

CA 2781273 A1 12/2013
EP 0305090 A2 8/1988
(Continued)

OTHER PUBLICATIONS

Hidajat et al., Quality characterisation of crude oils by partial least square calibration of NIR spectral profiles, Journal of Near Infrared Spectroscopy, vol. 8, No. 1, 2000, pp. 53-59 (Year: 2000).*
(Continued)

*Primary Examiner* — Toan M Le
*Assistant Examiner* — Xiuqin Sun
(74) *Attorney, Agent, or Firm* — Abelman, Frayne and Schwab (57) ABSTRACT

A system and a method for determining one or more distillation temperatures for one or more given distillation weight percentages of a crude oil sample are provided, which can be used to produce a simulated distillation curve. Simulated distillation temperatures of crude oil samples are assigned as a function of density and data derived from UV/Visible spectroscopy measurement of the crude oil samples.

20 Claims, 3 Drawing Sheets

(51) Int. Cl.
    *G01N 33/28*     (2006.01)
    *G01N 21/31*     (2006.01)
    *G01N 21/59*     (2006.01)

(52) U.S. Cl.
    CPC ......... *G01N 33/28* (2013.01); *G01N 33/2823* (2013.01); *G01N 2021/3155* (2013.01); *G01N 2201/12* (2013.01); *G01N 2201/129* (2013.01)

(58) Field of Classification Search
    CPC ....... G01N 2021/3155; G01N 2201/12; G01N 2201/129
    USPC .......................................................... 702/30
    See application file for complete search history.

(56) References Cited

U.S. PATENT DOCUMENTS

| | | | |
|---|---|---|---|
| 4,251,870 A | 2/1981 | Jaffe | |
| 4,897,177 A | 1/1990 | Nadler | |
| 4,971,915 A | 11/1990 | Schwartz et al. | |
| 4,988,446 A | 1/1991 | Haberman | |
| 5,121,337 A | 6/1992 | Brown | |
| 5,223,714 A | 6/1993 | Maggard | |
| 5,266,800 A | 11/1993 | Mullins | |
| 5,304,807 A | 4/1994 | Lin | |
| 5,424,959 A | 6/1995 | Reyes | |
| 5,452,232 A | 9/1995 | Espinosa et al. | |
| 5,475,612 A | 12/1995 | Espinosa | |
| 5,490,085 A | 2/1996 | Lambert et al. | |
| 5,572,030 A | 11/1996 | Ranson et al. | |
| 5,600,134 A | 2/1997 | Ashe et al. | |
| 5,602,755 A | 2/1997 | Ashe et al. | |
| 5,656,810 A | 8/1997 | Alfano et al. | |
| 5,699,269 A | 12/1997 | Ashe et al. | |
| 5,699,270 A | 12/1997 | Ashe et al. | |
| 6,070,128 A | 5/2000 | Descales | |
| 6,258,987 B1 | 7/2001 | Schmidt et al. | |
| 6,275,775 B1 | 8/2001 | Baco | |
| 6,490,029 B1 | 12/2002 | Cho | |
| 6,602,403 B1 | 8/2003 | Steffens et al. | |
| 6,611,735 B1 | 8/2003 | Henly | |
| 6,633,043 B2 | 10/2003 | Hegazi | |
| 6,662,116 B2 | 12/2003 | Brown | |
| 6,711,532 B1 | 3/2004 | Spieksma | |
| 6,841,779 B1 | 1/2005 | Roehner et al. | |
| 6,893,874 B2 | 5/2005 | Stark | |
| 7,126,332 B2 | 10/2006 | Blanz | |
| 7,173,239 B2 | 2/2007 | DiFoggio | |
| 7,560,711 B2 | 7/2009 | Hegazi | |
| 7,598,487 B2 | 10/2009 | Qian | |
| 8,714,246 B2 | 5/2014 | Pop et al. | |
| 8,930,149 B1 | 1/2015 | Koseoglu et al. | |
| 9,285,307 B2 | 3/2016 | Koseoglu et al. | |
| 9,423,391 B2 | 8/2016 | Koseoglu et al. | |
| 9,429,556 B2 | 8/2016 | Koseoglu et al. | |
| 9,778,240 B2 | 10/2017 | Koseoglu et al. | |
| 9,816,919 B2 | 11/2017 | Koseoglu et al. | |
| 2002/0052769 A1 | 5/2002 | Navani et al. | |
| 2003/0141459 A1 | 7/2003 | Hegazi et al. | |
| 2003/0195708 A1 | 10/2003 | Brown | |
| 2005/0109934 A1 | 5/2005 | David | |
| 2005/0173298 A1 | 8/2005 | Wellington | |
| 2006/0043004 A1 | 3/2006 | Rose | |
| 2006/0047444 A1 | 3/2006 | Brown | |
| 2006/0142955 A1 | 6/2006 | Jones | |
| 2007/0050154 A1 | 3/2007 | Albahri | |
| 2007/0231912 A1 | 10/2007 | Reischman et al. | |
| 2007/0295640 A1 | 12/2007 | Tan et al. | |
| 2008/0037006 A1 | 2/2008 | Canas Triana | |
| 2008/0040051 A1 | 2/2008 | Franklin et al. | |
| 2008/0206887 A1 | 8/2008 | Chen | |
| 2008/0248967 A1 | 10/2008 | Butler et al. | |
| 2008/0253426 A1 | 10/2008 | Voelkening | |
| 2008/0260584 A1 | 10/2008 | Gudde et al. | |
| 2009/0011517 A1 | 1/2009 | Hodges | |
| 2009/0180949 A1 | 7/2009 | Cui | |
| 2009/0279072 A1 | 11/2009 | Arakawa | |
| 2009/0290144 A1 | 11/2009 | Hegazi | |
| 2009/0316139 A1 | 12/2009 | Shrestha | |
| 2010/0049681 A1 | 2/2010 | Pradhan | |
| 2010/0113311 A1* | 5/2010 | Eccleston ............... G01M 3/20 |
| | | | 508/110 |
| 2010/0204925 A1 | 8/2010 | Albahri | |
| 2010/0211329 A1 | 8/2010 | Farquharson et al. | |
| 2010/0218585 A1 | 9/2010 | Chawla | |
| 2011/0152136 A1 | 6/2011 | Hughes et al. | |
| 2011/0308996 A1 | 12/2011 | Choudhary | |
| 2012/0171151 A1 | 7/2012 | Thomassian | |
| 2013/0209367 A1* | 8/2013 | Ito ........................ A61K 9/5153 |
| | | | 424/9.6 |
| 2014/0075827 A1 | 3/2014 | Gonzalez et al. | |
| 2014/0156241 A1 | 6/2014 | Kumar et al. | |
| 2015/0106027 A1 | 4/2015 | Koseoglu et al. | |
| 2015/0106028 A1 | 4/2015 | Koseoglu et al. | |
| 2015/0106029 A1 | 4/2015 | Koseoglu et al. | |
| 2015/0106031 A1 | 4/2015 | Koseoglu et al. | |
| 2015/0112610 A1 | 4/2015 | Koseoglu | |
| 2015/0112611 A1 | 4/2015 | Koseoglu | |
| 2016/0011102 A1 | 1/2016 | Koseoglu et al. | |
| 2016/0187253 A1 | 6/2016 | Koseoglu et al. | |
| 2016/0195481 A1 | 7/2016 | Koseoglu | |
| 2016/0195507 A1 | 7/2016 | Koseoglu | |
| 2016/0195508 A1 | 7/2016 | Al-Hajji | |
| 2016/0377589 A1 | 12/2016 | Koseoglu | |
| 2017/0003217 A1 | 1/2017 | Koseoglu | |
| 2017/0363540 A1 | 12/2017 | Koseoglu | |
| 2017/0363591 A1 | 12/2017 | Koseoglu | |
| 2017/0363602 A1 | 12/2017 | Koseoglu | |
| 2017/0363603 A1 | 12/2017 | Koseoglu | |

FOREIGN PATENT DOCUMENTS

| | | |
|---|---|---|
| EP | 0304232 A2 | 2/1989 |
| EP | 0552300 A1 | 7/1993 |
| EP | 0794433 A1 | 9/1997 |
| EP | 0859236 A1 | 8/1998 |
| EP | 0984277 A1 | 3/2000 |
| SU | 817486 A1 | 3/1981 |
| SU | 1523972 A1 | 11/1989 |
| WO | 03/048759 A1 | 6/2003 |
| WO | 2004033513 A2 | 4/2004 |
| WO | 2006030218 A1 | 3/2006 |
| WO | 2009082418 A2 | 7/2009 |
| WO | 2013102916 A1 | 7/2013 |

OTHER PUBLICATIONS

Adhvaryu, A. et al., Quantitative NMR Spectroscopy for the Prediction of Base Oil Properties, Tribology Transactions, vol. 43, No. 2, 2000, pp. 245-250.
Albahri, T. et al, Octane Number and Aniline Point of Petroleum Fuels, 2002, Fuel Chemistry Division, vol. 47(2), pp. 710-711.
Ali, M., Resolution and Quantification of Ring Type Aromatics by HPLC Method using N-Hexane Elution, 2003, King Fahd University of Petroleum and Minerals, pp. 1-9.
ASTM D2887-01, Standard Test Method for Boiling Range Distribution of Petroleum Fractions by Gas Chromatography, Annual Book of ASTM Standards, vol. 14, No. 02, pp. 204-216.
Birch C., Oil & Gas Journal, Jan. 14, 2002, pp. 54-59 (printed Jul. 9, 2014 from http://www.ogj.com/articles/print/volume-100/issue-2/processing/achieving-maximum-crude-oil-value-depends-on-accurate-evaluation.html).
Bowden, J. et al., Octane-Cetane Relationship, 1974, NTIS, p. 8.
Chemstations, Inc., Physical Properties User's Guide, 2004, Chemstations Inc., Ver. 5.4, pp. 18-22.
Cookson, D.J. et al., Investigation of the Chemical Basis of Diesel Fuel Properties, Energy & Fuels, vol. 2, No. 6, 1988, pp. 854-860.
Duvekot, C., Fast Analysis of Paraffins, iso-Paraffins, Olefins, iso-Olefins, Naphthenes and Aromatics in Hydrocarbon Streams, Varian, Inc., 2008, pp. 1-4.

(56) References Cited

OTHER PUBLICATIONS

Evokimov, I, et al, Potential of UV-Visible Absorption Spectroscopy for characterizing Crude Petroleum Oils, Oil an Gas Business, 2007, 21 pages.
Falla, F, et al., Characterization of crude petroleum by NIR, Journal of Petroleum Science and Engineering, vol. 51, 2006, pp. 127-137.
Fernandez-Lima, F. et al., Petroleum Crude Oil Characterization by IMS-MS and FTICR MS, 2009, American Chemical Society, Ed. 81, pp. 9941-9945.
Grizzle, P. et al., Automated Liquid Chromatographic Compound Class Group-Type Separation of Crude Oils and Bitumens Using Chemically Bonded Aminolilane, 1986, Publisher Anal. Chem., vol. 58, pp. 2389-2390.
Hasan, M.U. et al., Structural characterization of Saudi Arabian heavy crude oil by n.m.r. spectroscopy, Fuel, vol. 62, 1983, pp. 518-523.
Hidajat, K, et al., Quality characterisation of crude oils by partial least square calibration of NIR spectral profiles, Near Infrared Spectrosc, vol. 8, pp. 53-59, 2000.
Jokuty, P. et al., Hydrocarbon Groups and Their Relationships to Oil Properties and Behavior, 1995, Published by Whiticar Scientific, p. 11.
Khanmohammadi, M, et al., Characterization of petroleum-based products by infrared spectroscopyu and chemometrics, Trac Trends in Analytical Chem, vol. 35, 2012.
Kok, M, et al., High pressure TGA analysis of crude oils, Thermochimica Acta., vol. 287, No. 1, 1996, pp. 91-99.
Mckenna, Amy M., Heavy Petroleum Composition. 1. Exhaustive Compositional Analysis of Athabasca Bitumen HVGO Distillates by Fourier Transform Ion Cyclotron Resonance Mass Spectrometry: A Definitive Test of the Boduszynski Model, Energy Fuels, 24, 2010, pp. 2929-2038.
Mohammed, S., The Use of Compounds Chemically Related to Analyte as Surrogate Reference Standards in Quantitative HPLC, Feb. 2008, Produced by Kwame Nkrumah University of Science and Technology, Kumasi, p. 16.
Pande, S., et al., Cetana Number Predictions of a Trial Index Based on Compositional Analysis, American Chemical Society, 1989, pp. 308-312.
Patra, D, et al, Determination of Synchronous Fluorescence Scan Parameters for Certain Petroleum Products, Journal of Scientific & Industrial Research, Apr. 1, 2000, pp. 300-305.
Pavlovic K., Oil & Gas Journal, Nov. 22, 1999, pp. 51-56 (printed Jul. 9, 2014 from http://www.ogj.com/articles/print/volume-97/issue-47/in-this-issue/refining/gravity-and-sulfur-based-crude-valuations-more-accurate-than-believed.html).
Pereira,Thieres M. C., An evaluation of the aromaticity of asphaltenes using atmospheric pressure photoionization Fourier transform ion cyclotron resonance mass spectrometry—APP ($\pm$) FT-ICR MS, Fuel, 2014, vol. 118, 2014, pp. 348-357.
Rodgers, R. et al., Advanced Characterization of Petroleum Crude and Products by High Field Fourier Transform Ion Cyclotron Resonance Mass Spectrometry, 2002, Fuel Chemistry Division, Ed. 47(2), pp. 636-637.
Shea, T.M., Modeling Base Oil Properties using NMR Spectroscopy and Neural Networks, Tribology Transactions, vol. 46, No. 3, 2003, pp. 296-302.
Souza, C. et al., Cetane Number Assessment in Diesel Fuel by 1H or Hydrogen Nuclear Magnetic Resonance-Based Multivariate Calibration, Energy & Fuels, vol. 28, 2014, pp. 4958-4962.
Speight, Handbook of Petroleum Product Analysis, 2002.
Terra, L. et al., Petroleomics by electrospray ionization FT-ICR mass spectrometry coupled to partial least squares with variable selection methods: prediction of the total acid number of crude oils, 2014, Analyst, vol. 139, 2014, pp. 4908-4916.
University of Oldenburg, Institute of Physics, Catalogue of Optical Spectra of Oils, Jan. 2005, retrieved from http://las.physik.uni-oldenburg.de/data/spectra/indez.htm, 6 pages.
Yamashita, G.T., Evaluation of Integration Procedures for PNA Analysis by C-13 NMR, Symposium on Analytical Chemistry of Heavy Oils/Resids Presented Before the Division of Petroleum Chemistry, Inc., American Chemical Society, Dallas Meeting, Apr. 9-14, 1989, pp. 301-305.
PCT/US2016/012167, International Search Report and Written Opinion dated May 30, 2016, 18 pages.

\* cited by examiner

FIG. 3

# CHARACTERIZATION OF CRUDE OIL BY ULTRAVIOLET VISIBLE SPECTROSCOPY

RELATED APPLICATIONS

This application claims the benefit of U.S. Provisional Patent Application No. 62/099,669 filed Jan. 5, 2015, the disclosure of which is hereby incorporated by reference.

FIELD OF THE INVENTION

This invention relates to a method and process for the evaluation of samples of crude oil and its fractions by ultraviolet visible spectroscopy.

BACKGROUND OF THE INVENTION

Crude oil originates from the decomposition and transformation of aquatic, mainly marine, living organisms and/or land plants that became buried under successive layers of mud and silt some 15-500 million years ago. They are essentially very complex mixtures of many thousands of different hydrocarbons. Depending on the source, the oil predominantly contains various proportions of straight and branched-chain paraffins, cycloparaffins, and naphthenic, aromatic, and polynuclear aromatic hydrocarbons. These hydrocarbons can be gaseous, liquid, or solid under normal conditions of temperature and pressure, depending on the number and arrangement of carbon atoms in the molecules.

Crude oils vary widely in their physical and chemical properties from one geographical region to another and from field to field. Crude oils are usually classified into three groups according to the nature of the hydrocarbons they contain: paraffinic, naphthenic, asphaltic, and their mixtures. The differences are due to the different proportions of the various molecular types and sizes. One crude oil can contain mostly paraffins, another mostly naphthenes. Whether paraffinic or naphthenic, one can contain a large quantity of lighter hydrocarbons and be mobile or contain dissolved gases; another can consist mainly of heavier hydrocarbons and be highly viscous, with little or no dissolved gas. Crude oils can also include heteroatoms containing sulfur, nitrogen, nickel, vanadium and other elements in quantities that impact the refinery processing of the crude oil fractions. Light crude oils or condensates can contain sulfur in concentrations as low as 0.01 W %; in contrast, heavy crude oils can contain as much as 5-6 W %. Similarly, the nitrogen content of crude oils can range from 0.001-1.0 W %.

The nature of the crude oil governs, to a certain extent, the nature of the products that can be manufactured from it and their suitability for special applications. A naphthenic crude oil will be more suitable for the production of asphaltic bitumen, a paraffinic crude oil for wax. A naphthenic crude oil, and even more so an aromatic one, will yield lubricating oils with viscosities that are sensitive to temperature. However, with modern refining methods there is greater flexibility in the use of various crude oils to produce many desired type of products.

When produced at the well, crude oil is usually accompanied by variable amounts of sweet and sour gases, as well as formation brines having high total dissolved solids (TDS). The crude oil is usually stabilized and desalted soon after its production from a well.

A crude oil assay is a traditional method of determining the nature of crude oils for benchmarking purposes. Crude oils are subjected to true boiling point (TBP) distillations and fractionations to provide different boiling point fractions. The crude oil distillations are carried out using the American Standard Testing Association (ASTM) Method D 2892. The common fractions and their nominal boiling points are given in Table 1.

TABLE 1

| Fraction | Boiling Point, ° C. |
|---|---|
| Methane | −161.5 |
| Ethane | −88.6 |
| Propane | −42.1 |
| Butanes | −6.0 |
| Light Naphtha | 36-90 |
| Mid Naphtha | 90-160 |
| Heavy Naphtha | 160-205 |
| Light Gas Oil | 205-260 |
| Mid Gas Oil | 260-315 |
| Heavy Gas Oil | 315-370 |
| Light Vacuum Gas Oil | 370-430 |
| Mid Vacuum Gas Oil | 430-480 |
| Heavy Vacuum Gas Oil | 480-565 |
| Vacuum Residue | 565+ |

The yields, composition, physical and indicative properties of these crude oil fractions, where applicable, are then determined during the crude assay work-up calculations. Typical compositional and property information obtained in a crude oil assay is given in Table 2.

TABLE 2

| Property | Unit | Property Type | Fraction |
|---|---|---|---|
| Yield Weight and Volume % | W % | Yield | All |
| API Gravity | ° | Physical | All |
| Viscosity Kinematic @ 38° C. | ° | Physical | Fraction boiling >250° C. |
| Refractive Index @ 20° C. | Unitless | Physical | Fraction boiling <400° C. |
| Sulfur | W % | Composition | All |
| Mercaptan Sulfur, W % | W % | Composition | Fraction boiling <250° C. |
| Nickel | ppmw | Composition | Fraction boiling >400° C. |
| Nitrogen | ppmw | Composition | All |
| Flash Point, COC | ° C. | Indicative | All |
| Cloud Point | ° C. | Indicative | Fraction boiling >250° C. |
| Pour Point, (Upper) | ° C. | Indicative | Fraction boiling >250° C. |
| Freezing Point | ° C. | Indicative | Fraction boiling >250° C. |
| Microcarbon Residue | W % | Indicative | Fraction boiling >300° C. |
| Smoke Point, mm | mm | Indicative | Fraction boiling between 150-250 |

TABLE 2-continued

| Property | Unit | Property Type | Fraction |
|---|---|---|---|
| Octane Number | Unitless | Indicative | Fraction boiling <250° C. |
| Cetane Index | Unitless | Indicative | Fraction boiling between 150-400 |
| Aniline Point | ° C. | Indicative | Fraction boiling <520° C. |

Due to the number of distillation cuts and the number of analyses involved, the crude oil assay work-up is both costly and time consuming.

In a typical refinery, crude oil is first fractionated in the atmospheric distillation column to separate sour gas and light hydrocarbons, including methane, ethane, propane, butanes and hydrogen sulfide, naphtha (36°–180° C.), kerosene (180°–240° C.), gas oil (240°–370° C.) and atmospheric residue (>370° C.). The atmospheric residue from the atmospheric distillation column is either used as fuel oil or sent to a vacuum distillation unit, depending on the configuration of the refinery. The principal products obtained from vacuum distillation are vacuum gas oil, comprising hydrocarbons boiling in the range 370°–520° C., and vacuum residue, comprising hydrocarbons boiling above 520° C. The crude assay data help refiners to understand the general composition of the crude oil fractions and properties so that the fractions can be processed most efficiently and effectively in an appropriate refining unit.

In the field of organic chemistry, UV-visible spectrophotometry, which deals with electronic transitions within molecules, has traditionally provided unique information about aromatic and heteroaromatic compounds which absorb strongly in the UV region (200 nm-400 nm). Despite this and owing to the complex molecular nature of crude oil, UV-visible spectra of these oils are often described as featureless, poorly defined spectra.

New rapid and direct methods to help better understand crude oil composition and properties from the analysis of whole crude oil will save producers, marketers, refiners and/or other crude oil users substantial expense, effort and time. Therefore, a need exists for an improved system and method for determining properties of crude oil fractions from different sources and classifying the crude oil fractions based on their boiling point characteristics and/or properties.

SUMMARY OF THE INVENTION

Systems and methods for assigning one or more distillation temperatures for one or more given distillation weight percentages of a crude oil sample are provided, which can be used to produce a simulated distillation curve. Simulated distillation temperatures of crude oil samples are assigned as a function of density and data derived from UV/Visible spectroscopy measurement of the crude oil samples. The correlations also provide information about the gas oil indicative properties without fractionation/distillation (crude oil assays) and will help producers, refiners, and marketers to benchmark the oil quality and, as a result, valuate the oils without performing the customary extensive and time-consuming crude oil assays.

BRIEF DESCRIPTION OF THE DRAWING

Further advantages and features of the present invention will become apparent from the following detailed description of the invention when considered with reference to the accompanying drawings, in which.

DETAILED DESCRIPTION OF INVENTION

In the system and method herein, spectra are obtained by a suitable known or to be developed UV-visible spectrophotometry techniques. UV-visible spectrophotometry is carried out on a sample of crude oil according to the method and system herein to provide unique information about aromatic and heteroaromatic compounds which absorb strongly in the UV region (200 nm-400 nm). Specific individual aromatic compounds and components have maxima at well-defined wavelengths. Wavelength maxima of known aromatic compounds and components are evaluated and extracted from the UV spectra of crude oils. These maxima are used to formulate indices for the aromatic content of the crude oil. These indices can be used to obtain simulated distillation data for the oil sample. According to the provided method and system, this information is obtained relatively rapidly and inexpensively from a UV-visible scan as compared to the conventional assay methods.

A method for determining boiling point distribution of a hydrocarbon oil based upon UV/Visible spectroscopy data derived from a sample of the hydrocarbon oil and the density of the sample is provided. The sample is prepared for UV/Visible spectroscopy analysis. Spectra data for the sample is obtained by a UV/Visible spectroscopy analysis. The computer spectra data obtained by UV/Visible spectroscopy analysis of the sample is entered into a computer. Cumulative UV/Visible absorbance of the hydrocarbon oil from the UV/Visible spectroscopy data is calculated. The cumulative UV/Visible absorbance of the hydrocarbon oil is normalized to 100 W %. The wavelengths are determined at 0.5, 5, 10, 20, 30, 40, 50, 60, 70, 80, 90, 95, 99.5 W % points. The boiling point distribution of hydrocarbon oil is calculated from the normalized UV/Visible data and the density of hydrocarbon oil.

The system and method is applicable for naturally occurring hydrocarbons derived from crude oils, bitumens, heavy oils, shale oils and from refinery process units including hydrotreating, hydroprocessing, fluid catalytic cracking, coking, and visbreaking or coal liquefaction.

Figure 1:
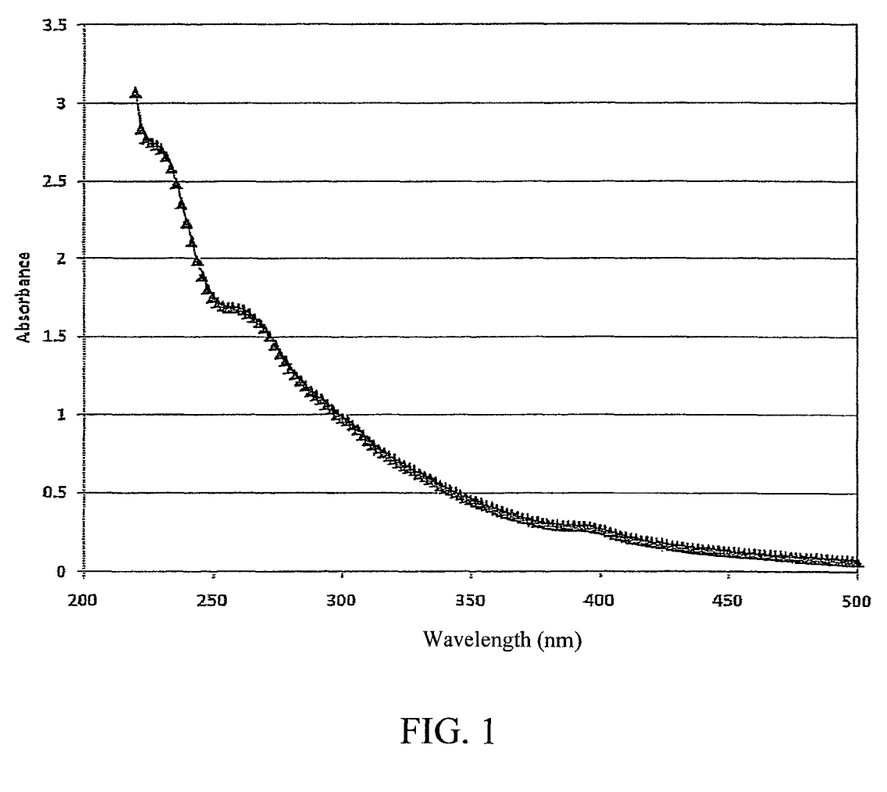
FIG. 1 is a graphic plot of typical ultraviolet visible spectroscopy data for a crude oil sample solution prepared as described herein.

FIG. 1 shows a process flowchart in a method according to one embodiment herein. Crude oil samples were prepared and analyzed by ultraviolet visible spectrophotometry between 200-500 nm, in certain embodiments between 220-400 nm. In step 210, the density of a crude oil sample is obtained.

In step 220, solutions are prepared by dissolving a sample of the crude oil in a two-part solvent system of a paraffinic solvent having from 5-20 carbon atoms and a polar solvent, e.g., at a ratio of 90:10% v/v. In certain embodiments, effective paraffinic solvents include iso-octane. In certain embodiments, effective polar solvents include dichloromethane.

The use of a polar solvent prevents precipitation of asphaltenes from the crude oil sample and ensures that all solutions are translucent for the measurement. The polar solvents are selected based on their Hildebrand solubility factors or their two-dimensional solubility parameters. The overall Hildebrand solubility factor is a well known measure of polarity and has been calculated for numerous compounds. See, for example, the Journal of Paint Technology, Vol. 39, No. 505 (February 1967). The solvents can also be described by their two-dimensional solubility parameter. See, for example, I. A. Wiehe, "Polygon Mapping with Two-Dimensional Solubility Parameters", *I&EC Research*, 34, 661-673 (1995). The complexing solubility parameter component, which describes the hydrogen bonding and electron donor-acceptor interactions, measures the interaction energy that requires a specific orientation between an atom of one molecule and a second atom of a different molecule. The field force solubility parameter, which describes the van der Waals and dipole interactions, measures the interaction energy of the liquid that is not destroyed by changes in the orientation of the molecules.

The UV absorbance of the crude oil solutions is determined, for instance, in a conventional one cm quartz cell. The absorbance values of the samples are summed at predetermined increments (e.g., even numbers, odd number, or increments of any number) between a predetermined range, e.g., between 200-500 nm, in certain embodiments between 220-400 nm.

In step 230, one or more samples of crude oil in dilute solution are analyzed by UV-visible spectrophotometry over the wavelengths 200-500 nm, in certain embodiments 220-400 nm.

In step 240, the density and spectra data are entered into a computer.

In step 250, the distillation temperature at a given distillation weight percentage is calculated as a function of the wavelength at known weight percent absorbance values and the density.

Equation (1) is used to calculate and assign a distillation temperature for a given distillation weight percentage:

$$T_{DT} = K_{SD} + X1_{SD}\left(\frac{1}{UVVWL}\right) + X2_{SD}\left(\frac{1}{DEN}\right) + X3_{SD}\left(\frac{1}{UVVWL^2}\right) + X4_{SD}\left(\frac{1}{DEN^2}\right) + X5_{SD}\left(\frac{1}{UVVWL*DEN}\right) X6_{SD}\left(\frac{1}{UVVWL^3}\right) + X7_{SD}\left(\frac{1}{DEN^3}\right) + X8_{SD}\left(\frac{1}{UVVWL^2*DEN}\right) + X9_{SD}\left(\frac{1}{DEN^2*UVVWL}\right); \quad (1)$$

where:

DT is the distillation weight percentage, $K_{SD}$, $X1_{SD}$, $X2_{SD}$, $X3_{SD}$, $X4_{SD}$, $X5_{SD}$, $X6_{SD}$, $X7_{SD}$, $X8_{SD}$ and $X9_{SD}$ are constants, DEN is the density of the sample (Kg/L), and UVVWL is the wavelength at DT.

Figure 2:
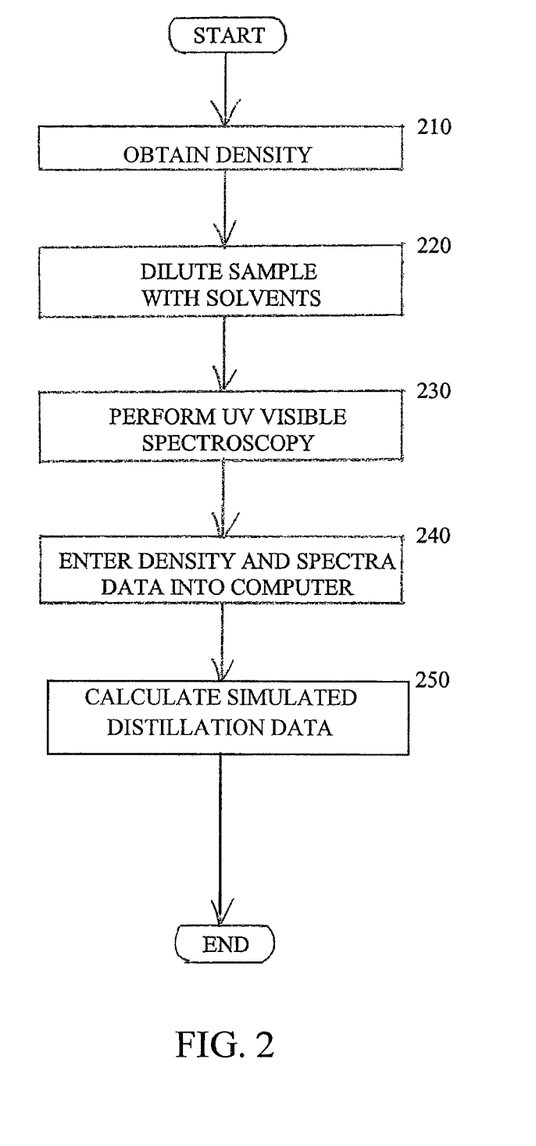
FIG. 2 is a process flow diagram of steps carried out to characterize distillation data of a crude oil sample, using the system and method herein.
Figure 3:
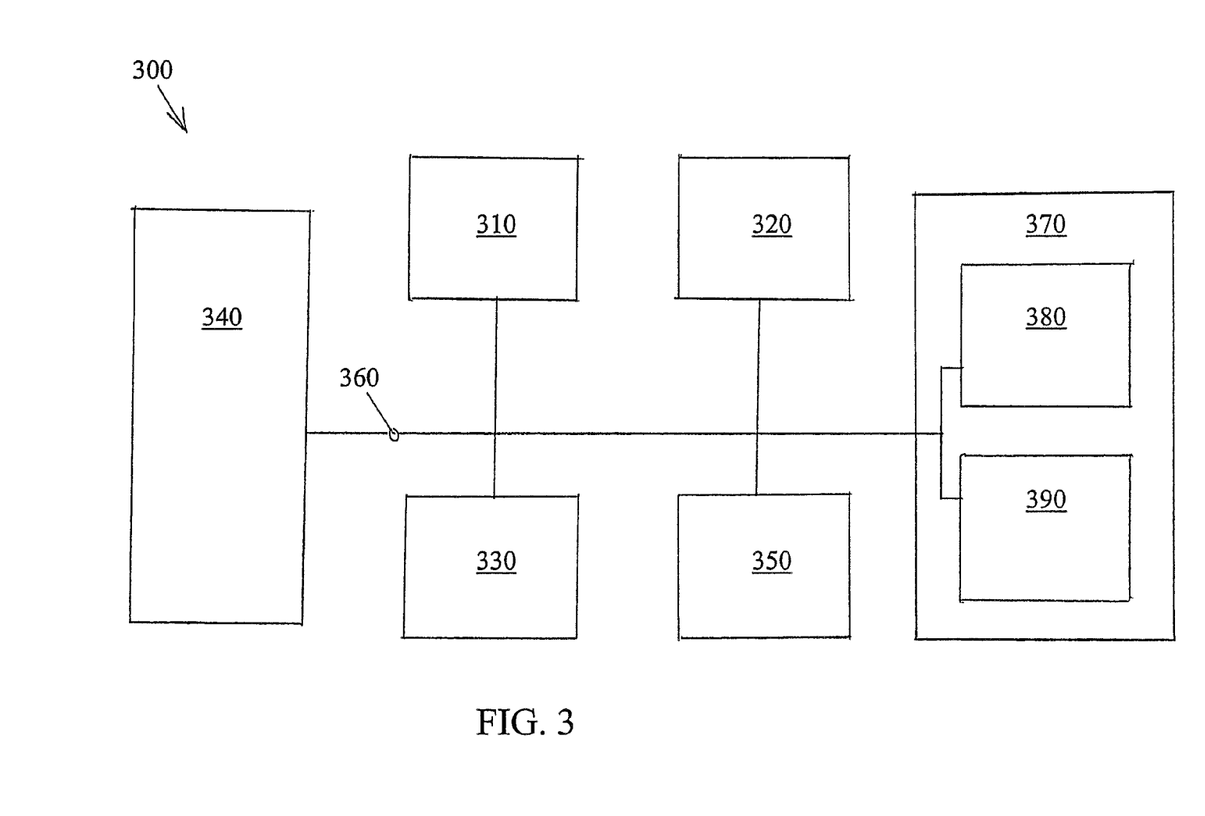
FIG. 3 is a block diagram of a component of a system for implementing the invention, according to one embodiment.

An exemplary block diagram of a computer system 300 by which the calculation modules can be implemented is shown in FIG. 2. Computer system 300 includes a processor 310, such as a central processing unit, an input/output interface 320 and support circuitry 330. In certain embodiments, where the computer 300 requires direct human interaction, a display 340 and an input device 350 such as a keyboard, mouse or pointer are also provided. The display 340, input device 350, processor 310, input/output interface 320 and support circuitry 330 are shown connected to a bus 360 which also connects to a memory unit 370. Memory 370 includes program storage memory 380 and data storage memory 390. Note that while computer 300 is depicted with the direct human interface components of display 340 and input device 350, programming of modules and importation and exportation of data can also be accomplished over the interface 320, for instance, where the computer 300 is connected to a network and the programming and display operations occur on another associated computer, or via a detachable input device, as are well known in the art for interfacing programmable logic controllers.

Program storage memory 380 and data storage memory 390 can each comprise volatile (RAM) and non-volatile (ROM) memory units and can also comprise hard disk and backup storage capacity, and both program storage memory 380 and data storage memory 390 can be embodied in a single memory device or separated in plural memory devices. Program storage memory 380 stores software program modules and associated data, and in particular stores calculation module(s) for obtaining the simulate distillation data. Data storage memory 390 stores data used and/or generated by the one or more modules of the present system, including density of the crude oil sample, UV absorbance data or portions thereof used by the one or more modules of the present system, and calculated data generated by the one or more modules of the present system.

The calculated and assigned results in accordance with the systems and methods herein are displayed, audibly outputted, printed, and/or stored to memory for use as described herein.

It is to be appreciated that the computer system 300 can be any general or special purpose computer such as a personal computer, minicomputer, workstation, mainframe, a dedicated controller such as a programmable logic controller, or a combination thereof. While the computer system 300 is shown, for illustration purposes, as a single computer unit, the system can comprise a group/farm of computers which can be scaled depending on the processing load and database size, e.g., the total number of samples that are processed and results maintained on the system. The computer system 300 can serve as a common multi-tasking computer.

The computing device 300 preferably supports an operating system, for example, stored in program storage memory 390 and executed by the processor 310 from volatile memory. According to the present system and method, the operating system contains instructions for interfacing the device 300 to the calculation module(s). According to an embodiment of the invention, the operating system contains instructions for interfacing computer system 300 to the Internet and/or to private networks.

Example

Table 3 is an example of a tabulation of values for the sample of Arab heavy crude oil in the wavelength range 220-400 nm. This data is depicted in the curve of FIG. 1.

TABLE 3

Absorbances of Arab Heavy Crude Oils at Wavelength Ranging from 220-400 nm at 2 nm Interval

| Wave Length | Absor., nm |
|---|---|
| 220 | 3.076 |
| 222 | 2.841 |
| 224 | 2.778 |
| 226 | 2.753 |
| 228 | 2.735 |
| 230 | 2.708 |
| 232 | 2.663 |
| 234 | 2.591 |
| 236 | 2.486 |
| 238 | 2.361 |
| 240 | 2.236 |
| 242 | 2.113 |
| 244 | 1.994 |
| 246 | 1.891 |
| 248 | 1.811 |
| 250 | 1.755 |
| 252 | 1.719 |
| 254 | 1.698 |
| 256 | 1.689 |
| 258 | 1.688 |
| 260 | 1.685 |
| 262 | 1.673 |
| 264 | 1.649 |
| 266 | 1.621 |
| 268 | 1.59 |
| 270 | 1.552 |
| 272 | 1.502 |
| 274 | 1.447 |
| 276 | 1.39 |
| 278 | 1.341 |
| 280 | 1.297 |
| 282 | 1.255 |
| 284 | 1.218 |
| 286 | 1.183 |
| 288 | 1.15 |
| 290 | 1.121 |
| 292 | 1.096 |
| 294 | 1.067 |
| 296 | 1.036 |
| 298 | 1.006 |
| 300 | 0.981 |
| 302 | 0.962 |
| 304 | 0.935 |
| 306 | 0.905 |
| 308 | 0.871 |
| 310 | 0.839 |
| 312 | 0.809 |
| 314 | 0.783 |
| 316 | 0.758 |
| 318 | 0.735 |
| 320 | 0.714 |
| 322 | 0.696 |
| 324 | 0.678 |
| 326 | 0.662 |
| 328 | 0.645 |
| 330 | 0.627 |
| 332 | 0.609 |
| 334 | 0.59 |
| 336 | 0.57 |
| 338 | 0.551 |
| 340 | 0.532 |
| 342 | 0.518 |
| 344 | 0.502 |
| 346 | 0.486 |
| 348 | 0.472 |
| 350 | 0.458 |
| 352 | 0.445 |
| 354 | 0.432 |
| 356 | 0.418 |
| 358 | 0.406 |
| 360 | 0.394 |
| 362 | 0.382 |
| 364 | 0.37 |
| 366 | 0.359 |
| 368 | 0.349 |
| 370 | 0.34 |
| 372 | 0.332 |
| 374 | 0.323 |
| 376 | 0.316 |
| 378 | 0.309 |
| 380 | 0.303 |
| 382 | 0.299 |
| 384 | 0.294 |
| 386 | 0.292 |
| 388 | 0.29 |
| 390 | 0.289 |
| 392 | 0.288 |
| 394 | 0.287 |
| 396 | 0.283 |
| 398 | 0.276 |
| 400 | 0.268 |

A crude oil sample with a density of 0.8828 kg/lt and the simulated distillation curve of 5 W %=94° C.; 10 W %=138° C.; 20 W %=204° C.; 30 W %=267° C.; 40 W %=326° C.; 50 W %=384° C.; 60 W %=446° C.; 70 W %=513° C.; 80 W %=592° C. was run at a UV/Visible spectrophotometer and a spectra was obtained in the wavelength range 220-500 nm. Cumulative UV/Visible absorbance of the sample was calculated from the UV/Visible spectra data and was normalized; a summary of % absorbances vs. wavelength was obtained using interpolation and/or numerical methods as follows:

5 W %=221 nm; 10 W %=225 nm; 20 W %=232 nm; 30 W %=240 nm; 40 W %=251 nm; 50 W %=263 nm; 60 W %=276; 70 W %=294; 80 W %=318 nm.

The following constant values were used to predict the temperature at 50 W % point, obtained by linear regression:

$K_{SD}$=1.683972E+04
$X1_{SD}$=2.995790E+07
$X2_{SD}$=−1.393801E+05
$X3_{SD}$=6.969095E+08
$X4_{SD}$=2.209817E+05
$X5_{SD}$=5.872777E+07
$X6_{SD}$=7.016542E+10
$X7_{SD}$=9.510150E+04
$X8_{SD}$=1.472998E+07
$X9_{SD}$=2.637995E+07

Using the above constants at a distillation weight percentage DT of 50%, the simulated distillation temperature at 50% distillation weight percentage is calculated and assigned as 412.4° C. The temperatures at 0.5, 5, 10, 20, 30, 40, 50, 60, 70, 80 W % points are calculated and compared with the actual data, and a perfect fit was obtained.

In alternate embodiments, the present invention can be implemented as a computer program product for use with a computerized computing system. Those skilled in the art will readily appreciate that programs defining the functions of the present invention can be written in any appropriate programming language and delivered to a computer in any form, including but not limited to: (a) information permanently stored on non-writeable storage media (e.g., read-only memory devices such as ROMs or CD-ROM disks); (b) information alterably stored on writeable storage media (e.g., floppy disks and hard drives); and/or (c) information conveyed to a computer through communication media, such as a local area network, a telephone network, or a public network such as the Internet. When carrying computer readable instructions that implement the present invention methods, such computer readable media represent alternate embodiments of the present invention.

As generally illustrated herein, the system embodiments can incorporate a variety of computer readable media that comprise a computer usable medium having computer readable code means embodied therein. One skilled in the art will recognize that the software associated with the various processes described can be embodied in a wide variety of computer accessible media from which the software is loaded and activated. Pursuant to *In re Beauregard*, 35 USPQ2d 1383 (U.S. Pat. No. 5,710,578), the present invention contemplates and includes this type of computer readable media within the scope of the invention. In certain embodiments, pursuant to *In re Nuijten*, 500 F.3d 1346 (Fed. Cir. 2007) (U.S. patent application Ser. No. 09/211,928), the scope of the present claims is limited to computer readable media, wherein the media is both tangible and non-transitory.

The system and method of the present invention have been described above and with reference to the attached figure; however, modifications will be apparent to those of ordinary skill in the art and the scope of protection for the invention is to be defined by the claims that follow.

We claim:

1. A system for assigning a simulated distillation temperature for a given distillation weight percentage to an oil sample based upon UV/Visible spectroscopy data, wherein the oil sample is selected from naturally occurring hydrocarbons derived from crude oils, bitumens, heavy oils or shale oils, wherein the oil sample is characterized by a density, wherein the oil sample is formed into an oil solution for spectroscopy, the system comprising:
a non-volatile memory device that stores calculation modules and data, the data including UV/Visible spectroscopy data indicative of absorbance peak intensity detected in a predetermined wavelength range for the oil sample;
a processor coupled to the memory;
a first calculation module that calculates and assigns a cumulative and normalized UV/Visible absorbance from the data indicative of absorbance values; and
a second calculation module that calculates and assigns a simulated distillation temperature for a given distillation weight percentage with a multi-variable polynomial equation with a set of predetermined constant coefficients developed using linear regression wherein the variables are the UV/Visible absorbance for the given distillation weight percentage, and the density of the oil sample.

2. The system as in claim 1, wherein plural distillation temperatures are assigned to obtain a set of simulated distillation data.

3. The system as in claim 1, wherein the given distillation weight percentage values are 0.5, 5, 10, 20, 30, 40, 50, 60, 70, 80 W %.

4. The system as in claim 1, wherein the simulated distillation temperature is calculated as $T_{DT}$ using the equation:

$$T_{DT} = K_{SD} + X1_{SD}\left(\frac{1}{UVVWL}\right) + \tag{1}$$

$$X2_{SD}\left(\frac{1}{DEN}\right) + X3_{SD}\left(\frac{1}{UVVWL^2}\right) + X4_{SD}\left(\frac{1}{DEN^2}\right) +$$

$$X5_{SD}\left(\frac{1}{UVVWL*DEN}\right) X6_{SD}\left(\frac{1}{UVVWL^3}\right) + X7_{SD}\left(\frac{1}{DEN^3}\right) +$$

$$X8_{SD}\left(\frac{1}{UVVWL^2*DEN}\right) + X9_{SD}\left(\frac{1}{DEN^2*UVVWL}\right);$$

where:
DT is the distillation weight percentage, $K_{SD}$, $X1_{SD}$, $X2_{SD}$, $X3_{SD}$, $X4_{SD}$, $X5_{SD}$, $X6_{SD}$, $X7_{SD}$, $X8_{SD}$ and $X9_{SD}$ are constants, DEN is the density of the sample (Kg/L), and UVVWL is the wavelength at DT.

5. A system for assigning a simulated distillation temperature for a given distillation weight percentage to an oil sample, wherein the oil sample is selected from naturally occurring hydrocarbons derived from crude oils, bitumens, heavy oils or shale oils, wherein the oil sample is characterized by a density, wherein the oil sample is formed into an oil solution for spectroscopy, the system comprising:
an ultraviolet visible spectrometer that outputs ultraviolet visible spectroscopy data derived from the oil sample,
a non-volatile memory device that stores calculation modules and data, the data including UV/Visible spectroscopy data indicative of absorbance peak intensity detected in a predetermined wavelength range for the oil sample;
a processor coupled to the memory;
a first calculation module that calculates and assigns a cumulative and normalized UV/Visible absorbance from the data indicative of absorbance values; and
a second calculation module that calculates and assigns a simulated distillation temperature for a given distillation weight percentage with a multi-variable polynomial equation with a set of predetermined constant coefficients developed using linear regression wherein the variables are the UV/Visible absorbance for the given distillation weight percentage, and the density of the oil sample.

6. The system as in claim 5, wherein the oil sample is crude oil.

7. The system as in claim 5, wherein the oil sample is obtained from an oil well, stabilizer, extractor, or distillation tower.

8. The system as in claim 5, wherein plural distillation temperatures are assigned to obtain a set of simulated distillation data.

9. The system as in claim 5, wherein the given distillation weight percentage values are 0.5, 5, 10, 20, 30, 40, 50, 60, 70, 80 W %.

10. The system as in claim 5, wherein the simulated distillation temperature is calculated as $T_{DT}$ using the equation:

$$T_{DT} = K_{SD} + X1_{SD}\left(\frac{1}{UVVWL}\right) + \tag{1}$$

$$X2_{SD}\left(\frac{1}{DEN}\right) + X3_{SD}\left(\frac{1}{UVVWL^2}\right) + X4_{SD}\left(\frac{1}{DEN^2}\right) +$$

$$X5_{SD}\left(\frac{1}{UVVWL*DEN}\right) X6_{SD}\left(\frac{1}{UVVWL^3}\right) + X7_{SD}\left(\frac{1}{DEN^3}\right) +$$

$$X8_{SD}\left(\frac{1}{UVVWL^2*DEN}\right) + X9_{SD}\left(\frac{1}{DEN^2*UVVWL}\right);$$

where:
DT is the distillation weight percentage, $K_{SD}$, $X1_{SD}$, $X2_{SD}$, $X3_{SD}$, $X4_{SD}$, $X5_{SD}$, $X6_{SD}$, $X7_{SD}$, $X8_{SD}$ and $X9_{SD}$ are constants, DEN is the density of the sample (Kg/L), and UVVWL is the wavelength at DT.

11. A method for operating a computer to assign a simulated distillation temperature for a given distillation weight percentage to a fraction of an oil sample based upon near infrared spectroscopy data, wherein the oil sample is selected from naturally occurring hydrocarbons derived from crude oils, bitumens, heavy oils or shale oils, wherein the oil sample is characterized by a density, wherein the oil sample is formed into an oil solution for spectroscopy, the method comprising:
 entering into the computer UV/Visible spectroscopy data indicative of absorbance peak intensity detected in a predetermined wavelength range for the oil sample;
 calculating and assigning a cumulative and normalized UV/Visible absorbance from the data indicative of absorbance values; and
 calculating and assigning a simulated distillation temperature for a given distillation weight percentage with a multi-variable polynomial equation with a set of predetermined constant coefficients developed using linear regression wherein the variables are the UV/Visible absorbance for the given distillation weight percentage, and the density of the oil sample.

12. The method as in claim 11, wherein plural distillation temperatures are assigned to obtain a set of simulated distillation data.

13. The method as in claim 11, wherein the given distillation weight percentage values are 0.5, 5, 10, 20, 30, 40, 50, 60, 70, 80 W %.

14. The method as in claim 11, wherein the simulated distillation temperature is calculated as $T_{DT}$ using the equation:

$$T_{DT} = K_{SD} + X1_{SD}\left(\frac{1}{UVVWL}\right) + X2_{SD}\left(\frac{1}{DEN}\right) + X3_{SD}\left(\frac{1}{UVVWL^2}\right) + X4_{SD}\left(\frac{1}{DEN^2}\right) + X5_{SD}\left(\frac{1}{UVVWL*DEN}\right) X6_{SD}\left(\frac{1}{UVVWL^3}\right) + X7_{SD}\left(\frac{1}{DEN^3}\right) + X8_{SD}\left(\frac{1}{UVVWL^2*DEN}\right) + X9_{SD}\left(\frac{1}{DEN^2*UVVWL}\right); \quad (1)$$

where:
DT is the distillation weight percentage, $K_{SD}$, $X1_{SD}$, $X2_{SD}$, $X3_{SD}$, $X4_{SD}$, $X5_{SD}$, $X6_{SD}$, $X7_{SD}$, $X8_{SD}$ and $X9_{SD}$ are constants, DEN is the density of the sample (Kg/L), and UVVWL is the wavelength at DT.

15. A method for assigning a simulated distillation temperature for a given distillation weight percentage to a fraction of an oil sample, wherein the oil sample is selected from naturally occurring hydrocarbons derived from crude oils, bitumens, heavy oils or shale oils, wherein the oil sample is characterized by a density, wherein the oil sample is formed into an oil solution for spectroscopy, the method comprising:
 obtaining UV/Visible spectroscopy data indicative of absorbance peak intensity detected in a predetermined wavelength range for the oil sample;
 entering into a computer the obtained UV/Visible spectroscopy data;
 calculating and assigning a cumulative and normalized UV/Visible absorbance from the data indicative of absorbance values; and
 calculating and assigning a simulated distillation temperature for a given distillation weight percentage with a multi-variable polynomial equation with a set of predetermined constant coefficients developed using linear regression wherein the variables are the UV/Visible absorbance for the given distillation weight percentage, and the density of the oil sample.

16. The method as in claim 15, wherein the oil sample is crude oil.

17. The method as in claim 15, wherein the oil sample is obtained from an oil well, stabilizer, extractor, or distillation tower.

18. The method as in claim 15, wherein plural distillation temperatures are assigned to obtain a set of simulated distillation data.

19. The method as in claim 15, wherein the given distillation weight percentage values are 0.5, 5, 10, 20, 30, 40, 50, 60, 70, 80 W %.

20. The method as in claim 15, wherein the simulated distillation temperature is calculated as $T_{DT}$ using the equation:

$$T_{DT} = K_{SD} + X1_{SD}\left(\frac{1}{UVVWL}\right) + X2_{SD}\left(\frac{1}{DEN}\right) + X3_{SD}\left(\frac{1}{UVVWL^2}\right) + X4_{SD}\left(\frac{1}{DEN^2}\right) + X5_{SD}\left(\frac{1}{UVVWL*DEN}\right); \quad (1)$$

where:
DT is the distillation weight percentage, $K_{SD}$, $X1_{SD}$, $X2_{SD}$, $X3_{SD}$, $X4_{SD}$, $X5_{SD}$, $X6_{SD}$, $X7_{SD}$, $X8_{SD}$ and $X9_{SD}$ are constants, DEN is the density of the sample (Kg/L), and UVVWL is the wavelength at DT.

* * * * *